United States Patent [19]

Abeler

[11] Patent Number: 5,021,491

[45] Date of Patent: Jun. 4, 1991

[54] ORGANOTIN ALKOXYCARBONYLPHENYL MERCAPTIDES AND THE USE THEREOF

[75] Inventor: Gerd Abeler, Darmstadt, Fed. Rep. of Germany

[73] Assignee: Ciba-Geigy Corporation, Ardsley, N.Y.

[21] Appl. No.: 488,483

[22] Filed: Mar. 1, 1990

Related U.S. Application Data

[63] Continuation of Ser. No. 385,938, Jul. 21, 1989, abandoned, which is a continuation of Ser. No. 278,875, Dec. 2, 1988, abandoned.

[30] Foreign Application Priority Data

Dec. 17, 1987 [CH] Switzerland ............................ 4924/87

[51] Int. Cl.$^5$ .......................... C08K 5/58; C07F 7/22
[52] U.S. Cl. ........................................ 524/180; 556/93
[58] Field of Search ........................ 524/177, 180, 181; 556/93

[56] References Cited

U.S. PATENT DOCUMENTS

| | | | |
|---|---|---|---|
| 2,648,650 | 8/1953 | Weinberg et al. | 556/93 |
| 2,713,585 | 7/1955 | Best | 556/93 |
| 2,731,482 | 1/1956 | Stefl et al. | 556/93 |
| 2,731,484 | 1/1956 | Best | 556/93 |
| 3,507,827 | 4/1970 | Pollock | 524/180 |
| 3,640,947 | 2/1972 | Gloskey | 524/181 |
| 3,803,083 | 4/1974 | Brecker | 524/180 |
| 3,943,099 | 3/1976 | Bakassian et al. | 524/181 |
| 4,041,014 | 8/1977 | Mack | 524/181 |
| 4,146,518 | 3/1979 | Minagawa et al. | 524/180 |
| 4,179,432 | 12/1979 | Molt | 524/181 |
| 4,314,934 | 2/1982 | Smith | 524/180 |
| 4,554,368 | 11/1985 | Maul et al. | 556/91 |

Primary Examiner—Veronica P. Hoke
Attorney, Agent, or Firm—JoAnn Villamizar

[57] ABSTRACT

Compounds of the formula I

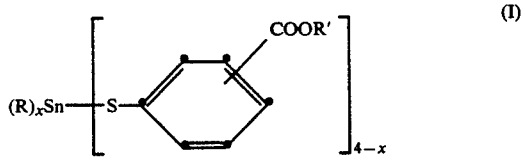

in which R is $C_8$-$C_{14}$alkyl, phenyl, $C_7$-$C_9$aralkyl or R"OOC-$CH_2$-$CH_2$, R' is $C_2$-$C_{18}$alkyl, $C_5$-$C_{12}$cycloalkyl, phenyl, $C_7$-$C_{30}$alkaryl or $C_7$-$C_{18}$-aralkyl and R" is $C_1$-$C_{14}$alkyl, phenyl or $C_7$-$C_9$aralkyl and x is 1 or 2, are heat stabilizers for chlorine-containing thermoplastics, in particular for PVC.

14 Claims, No Drawings

ORGANOTIN ALKOXYCARBONYLPHENYL MERCAPTIDES AND THE USE THEREOF

This application is a continuation of application Ser. No. 385,938, filed July 21, 1989, which is a continuation of Ser. No. 278,875 filed Dec. 12, 1988, all now abandoned.

The present invention relates to novel organotin alkoxycarbonylphenyl mercaptides and the use thereof for stabilizing chlorine-containing thermoplastics against the harmful effect of light and heat.

Organotin mercaptides of the formula $$R_xSn(SR')_{4-x}$$

in which, for example, R' can be 2-mercaptomethylbenzoate and $R_2$ can be alkyl or aryl, and x has the values 1 or 2, are known from U.S. Pat. Specification Nos. 2,731,482 and 2,731,484 and also 2,713,585.

Compounds of the formula $R_2Sn(SR'COOR'')_2$ are known from U.S. Pat. Specification No. 2,648,650 and, in particular, the compound dibutyltin S,S'-bis(methylthiosalicylate) is described in Example XVI.

U.S. Pat. Specification No. 3,507,827 describes compounds of the formula $R_1R_2Sn(S-Z_1-(COOR_3)_m)_2$ in which the $-S-Z_1-(COOR_3)$ group can be derived, for example, from a mercaptobenzoic acid ester.

Again, diorganotin mercaptides prepared by condensation of a diorganotin oxide or chloride with monohydric or polyhydric mercaptans belonging to the class of compounds of mercaptocarboxylic acid esters are known in general from German Offenlegungsschrift No. 2,447,499.

The use of organotin compounds of the general formula $$R-\underset{\underset{X^1}{|}}{\overset{\overset{R^1}{|}}{Sn}}-X_p$$

in which R and $R^1$ can be, for example, alkyl, aryl, aralkyl or alkaryl and X and $X^1$ can be, for example, $$-S\text{-Arylen-}\overset{\overset{O}{\|}}{C}-O-R^8$$

in which $R^8$ can be alkyl, aryl, aralkyl, alkaryl and the like, for stabilizing halogen-containing polymers together with mercaptophenols is suggested in U.S. Pat. Specification No. 4,314,934.

Furthermore, a generic formula for organotin mercaptides $$R_nSn(SR^1COOR^2)_{4-n'}$$

in which R can be alkyl, aryl and the like, $R^1$ can be, for example, arylene and $R^2$ can be an alkyl or aryl group and the like can be inferred from German Offenlegungsschrift No. 2,639,086. The further teaching of this patent specification is the combination of hydroxybenzophenones with organotin sulfur compounds for stabilizing polyolefins against the harmful effects of light and/or heat.

The methyltin, butyltin and tert-butyltin compounds together with the methyl, ethyl, butyl and iso-butyl esters of thiosalicylic acid are explicitly disclosed in the state of the art mentioned above.

However, these organotin mercapto compounds which have been disclosed have never gained acceptance in the industry. The reason for this may, for example, be that, in spite of their generally very high effectiveness, the organotin sulfur stabilizers cannot meet all the requirements. Their possible use is restricted, for example, if a high resistance to light and weathering in the finished article is desired. A further restriction in the field of plasticized PVC can arise if very strict requirements regarding the odour of the finished article are set, as is desirable in interior spaces, for example those of motor vehicles. In the case of mineral water free from carbonic acid organotin-stabilized rigid PVC bottles have proved inappropriate, because it is not possible to exclude impairment of the taste of the contents. Stabilization by means of calcium/zinc stabilizers has therefore proved successful in this sector, although, from a technical point of view, the tin stabilizers would have been desirable because of their higher effectiveness.

The discovery of novel organotin stabilizers having improved organoleptic properties is, therefore, urgently desired, but is only of technical importance if the pattern of properties in other respects, such as outstanding effectiveness, good compatibility with the substrate, low rheological effect on the moulding material, low tendency to plate out during processing and absence of toxicity, is also present.

It has now been found that certain organotin (carboalkoxy)phenyl mercaptides have a particularly advantageous effect on the odour characteristics of stabilized, chlorine-containing polymers in the thermoplastic processing and the subsequent use of the moulding materials prepared therefrom, with the retention of the advantageous properties for this class of stabilizers.

The invention relates to compounds of the formula I $$-HC(CH_2)_aCH_2$$

$$(R)_xSn\left[-S-\underset{}{\underset{}{\bigcirc}}-COOR'\right]_{4-x} \quad (I)$$

in which R is $C_8-C_{14}$alkyl, phenyl, $C_7-C_9$aralkyl or $R''OOC-CH_2-CH_2-$, R' is $C_2-C_{18}$alkyl, $C_5-C_{12}$cycloalkyl, phenyl, $C_7-C_{30}$alkaryl or $C_7-C_{18}$aralkyl and R'' is $C_1-C_{14}$alkyl, phenyl or $C_7-C_9$aralkyl and x is 1 or 2, subject to the proviso that, if x is 1, the group COOR' is not located in the orthoposition relative to the mercapto group.

Examples of R as $C_8-C_{14}$alkyl are octyl, 2-ethylhexyl (iso-octyl), nonyl, decyl, undecyl, dodecyl, tridecyl or tetradecyl.

Examples of R as $C_7-C_9$aralkyl are benzyl, methylbenzyl or hydroxybenzyl.

Examples of R' as $C_2-C_{18}$alkyl are ethyl, propyl, isopropyl, butyl, isobutyl, 2-butyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, octadecyl or heptadecyl.

An example of R' as $C_5$-$C_{12}$cycloalkyl is a cycloalkyl group of the formula —HC(CH$_2$)$_a$CH$_2$ in which a is an integer from 3 to 10.

This cycloalkyl group can be unsubstituted or substituted by $C_1$-$C_4$alkyl. Examples of this are cyclopentyl, cyclohexyl, methylcyclohexyl, dimethylcyclohexyl, trimethylcyclohexyl, t-butylcyclohexyl, cyclooctyl and cyclododecyl. Cyclohexyl which is unsubstituted or substituted by $C_1$-$C_4$alkyl is particularly preferred.

As $C_7$-$C_{30}$alkaryl, R' can be, for example, tolyl, xylyl, 4-t-butylphenyl, 3-methoxyphenyl, 4-propoxyphenyl, 3-butoxycarbonylphenyl, 3-nitrophenyl or 4-methyl-3-nitrophenyl or can be phenyl which is substituted by alkoxycarbonyl in which alkoxy can be, for example, methoxy, ethoxy, isopropoxy or n-butoxy.

As $C_7$-$C_{18}$aralkyl, R' can be $C_7$-$C_{10}$phenylalkyl which is unsubstituted or substituted on the phenyl ring by $C_1$-$C_4$alkyl and/or OH. Examples of this are benzyl, methylbenzyl, hydroxybenzyl, 3,5-di-t-butyl-4-hydroxybenzyl and 2-(3,5-di-t-butyl-4-hydroxyphenyl)-ethyl. Substituted or unsubstituted benzyl is preferred.

Examples of R" as $C_1$-$C_{14}$alkyl are methyl, ethyl, propyl, isopropyl, butyl, isobutyl, t-butyl, pentyl, hexyl, heptyl, octyl, 2-ethylhexyl, decyl or dodecyl. Linear or branched $C_1$-$C_4$alkyl is preferred.

Examples of R" as $C_7$-$C_9$aralkyl are benzyl, methylbenzyl or hydroxybenzyl.

Compounds of the formula I in which R is alkyl having 8 to 12 C atoms or is carbo-$C_2$-$C_5$alkoxyethyl are advantageous. R is preferably iso-octyl, dodecyl or carbobutoxyethyl. The advantageous compounds of the formula I also include those in which R' is alkyl having 2 to 12, preferably 2 to 8, C atoms.

The esterified acid group on the phenylene radical can be located in the ortho-, meta- or para-position relative to the mercapto group; the orthoposition or para-position is advantageous. This is subject to the proviso that, of the monoalkyltin triscarboalkoxyphenyl mercaptides, only the corresponding meta-mercaptobenzoic and para-mercaptobenzoic acid esters are embraced by the present invention, and the corresponding ortho-mercaptobenzoic acid esters are excluded.

However, the preferred compounds of the formula I include those in which the esterified acid group on the phenyl radical is located in the orthoposition relative to the mercapto group and which have the formula

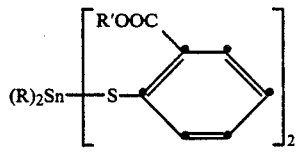

A particularly preferred compound has the formula

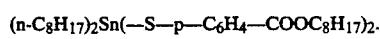

The preparation of the compounds of the formula I in which x is 2 can be effected by methods which are known per se, by reacting suitable organotin compounds with appropriate mercaptobenzoic acid esters. Suitable organotin compounds are, in particular, diorganotin oxides which react, with liberation of water, to give the compounds of the formula I.

Diorganotin halides, in particular dialkyltin dichlorides which require the addition of hydrogen halide acceptors for complete reaction to give the dimercaptides are also suitable. The best results can be achieved with the following basic reagents, subject to the requirement that saponification of the ester groups is prevented by careful control of the pH during the reaction: oxides, hydroxides, for example sodium hydroxide, carbonates, for example Na carbonate or K carbonate, or tertiary amines, for example triethylamine. The processes of preparation mentioned are illustrated by means of the following equations.

The reaction scheme of the process for the preparation of the mercapto derivatives, using, for example, an organotin oxide as the starting material, is represented by the following equation:

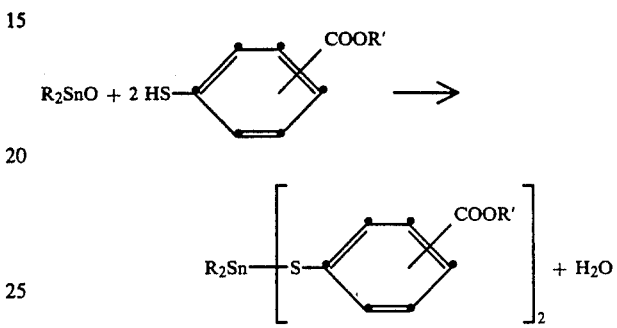

Using a diorganotin chloride as the starting material, the equation is as follows:

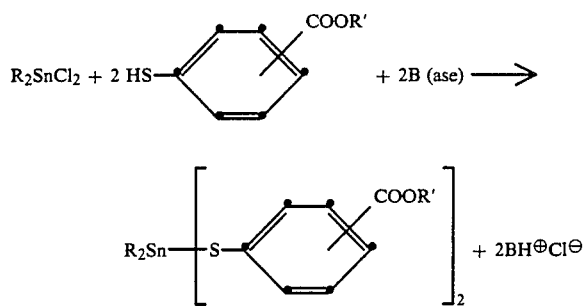

m-Mercaptobenzoic and p-mercaptobenzoic acid esters can be reacted analogously with monoorganotin oxides or halides to five compounds of the general formula I in which x is 1.

For the reaction of stannonic acid or a monoorganotin chloride with the mercapto compound the equation is as follows:

RSnOOOH bzw. RSnCl$_3$ +

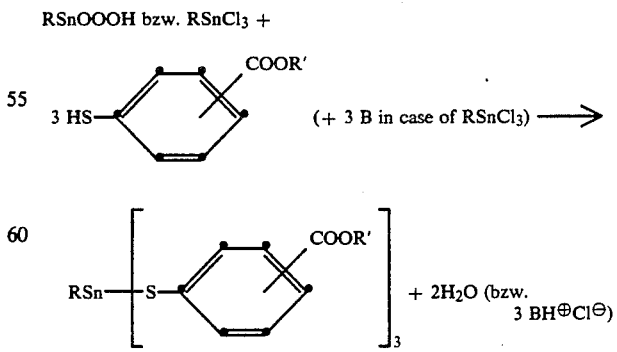

If water is liberated in the reaction from the condensation of the acid with the oxide or hydroxide, the reaction is carried out, for example, in vacuo at an elevated temperature of up to approx. 100° C. in order to remove continuously the water formed during the reaction.

If organotin halides are used, it is advantageous to carry out the reaction in the presence of water and a basic substance in order to fix and neutralize the hydrohalic acid which is formed. The temperature in this reaction is not critical and can preferably be kept between room temperature and 40° C.

If desired, the reaction can also be carried out in inert solvents. Examples of such solvents are toluene, benzene, methyl alcohol, petroleum ether, xylene and the like or chlorinated hydrocarbons, such as carbon tetrachloride, trichloroethylene, tetrachloroethylene, hexachlorobutadiene and the like. Two-phase systems composed of inert organic solvents and water are also advantageous as the reaction medium in certain cases.

The processes of preparation mentioned make it possible to use the starting materials in stoichiometric ratios, that is to say without the necessity of adding an excess of one or the other component.

The starting materials are converted essentially quantitatively into the end products, which, in turn, can be obtained in almost quantitative yields.

The organotin (carboalkoxy)-phenyl mercaptides of the formula I according to the invention can be used as stabilizers for chlorine-containing thermoplastics, for example for polymers and copolymers of vinyl chloride, vinylidene chloride, chlorinated polyolefins, post-chlorinated polyvinyl chloride or chlorinated rubbers. The stabilization of polyvinyl chloride (PVC) and moulding materials containing polyvinyl chloride is of particular importance. This can be suspension PVC, emulsion PVC or bulk polymers.

The halogen-containing plastics which are protected against heat and light by the stabilizers according to the present invention thus include polymers of vinyl chloride and vinyl resins containing vinyl chloride units in their structure, for example copolymers of vinyl chloride with vinyl esters of aliphatic acids, in particular vinyl acetate; copolymers of vinyl chloride with esters of acrylic and methacrylic acid and copolymers with acrylonitrile; copolymers of vinyl chloride with diene compounds and unsaturated dicarboxylic acids or anhydrides thereof, such as copolymers of vinyl chloride with diethyl maleate, diethyl fumarate or maleic anhydride; also post-chlorinated polymers and copolymers of vinyl chloride; copolymers of vinyl chloride and of vinylidene chloride with unsaturated aldehydes, ketones and other compounds, such as acrolein, crotonaldehyde, vinyl methyl ketene, vinyl methyl ether, vinyl isobutyl ether and the like; polymers of vinylidene chloride and copolymers thereof with vinyl chloride and other polymerizable compounds; polymers of vinyl chloroacetate and of dichlorodivinyl ether; chlorinated polymers of vinyl acetate; chlorinated polymeric esters of acrylic acid and of α-substituted acrylic acids; polymers of chlorinated styrenes, such as dichlorostyrene; chlorinated rubber and chlorinated ethylene polymers; polymers and post-chlorinated polymers of chlorobutadiene and copolymers thereof with vinyl chloride; rubber hydrochlorides and chlorinated rubber hydrochlorides; and also mixtures of the polymers mentioned with one another or with other polymerizable compounds. The corresponding bromides and fluorides of the compounds mentioned are embraced analogously by the groups of compounds enumerated.

Mixtures of the homopolymers and copolymers mentioned above, in particular vinyl chloride homopolymers, with other thermoplastic and/or elastomeric polymers, in particular with ABS, MBS, NBR, NAR, SAN, EVA and modified EVA, are also preferred substrates. So, finally, are also the mixtures of vinyl chloride homopolymer with plasticizers and/or copolymer resins in which the vinyl chloride polymer is present to the extent of 20 - 80% by weight and the plasticizers can be, for example, esters of phthalic acid, adipic acid or benzenetricarboxylic acids.

The compounds of the formula I can be added to the chlorine-containing thermoplastics in an amount of, for example, 0.1 to 5% by weight, relative to the thermoplastics. It is preferable to use 0.5 to 3% by weight. It is also possible to use mixtures of two or more compounds of the formula I in this connection. It is then preferable to use at least one monoorganotin compound and at least one diorganotin compound according to formula I.

The use of mixtures of diorganotin compounds according to formula I and other stabilizers (co-stabilizers), for example other organotin stabilizers, preferably a mixed dialkyltin carboxylate, as a stabilizer for the chlorine-containing thermoplastics is also of importance and can be regarded as a preferred use form.

Finally, in addition to at least one compound of the formula I according to the present invention, a stabilized thermoplastic can also contain other co-stabilizers, in particular one from the list given below, it being possible for the ratio by weight of stabilizer according to formula I to co-stabilizers to be from 60 to 40 up to 97 to 3.

The ratio by weight of stabilizer according to formula I to co-stabilizer from the series of the dialkyltin carboxylates is preferably from 60 to 40 up to 90 to 10.

The preferred dialkyltin carboxylates are dialkyltin bis-carboxylates and basic dialkyltin carboxylates of the formula $R_2Sn(OOCR')_2$ or $[R_2Sn(OOCR')]_2O$ and, for example, dioctyltin bis-caprylate, dioctyltin bis-laurate, basic dioctyltin bis-i-stearate and dibutyltin bis-i-octoate.

The stabilizers according to the invention can be incorporated into the polymeric substrates by the customary processes for incorporating additives into thermoplastics, for example by mixing in the form of powder and subsequent shaping processing or by being added on a roll mill or in a kneader. It is possible to incorporate at the same time the other additives such as are customary in the technology of chlorine-containing thermoplastics, for example the slip agents, plasticizers, fillers, impact strength additives, pigments, light stabilizers or antioxidants or the other heat stabilizers, for example metal carboxylates or organic phosphites.

Other co-stabilizers which can be used can be taken from the list below.

The stabilizers according to the invention can also be employed advantageously in combination, in customary ratios, with at least one of the conventional PVC stabilizers and/or other additives, such as epoxy compounds, phosphites, metal carboxylates and metal phenates of metals of the second main group and sub-group of the periodic system, or inorganic salts of metals of the second sub-group of the periodic system, for example $ZnCl_2$, and also antioxidants.

Co-stabilizers are preferably incorporated in amounts of 0.05 to 6, in particular 0.1 to 3% by weight, relative to the whole composition.

Suitable conventional phosphites are phosphites of the general formula

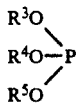

in which $R_3$, $R_4$ and $R_5$ are identical or different and are $C_6$-$C_{18}$alkyl, $C_6$-$C_{18}$alkenyl, a substituted or unsubstituted phenyl radical or $C_5$-$C_7$-cycloalkyl.

Examples of $R_3$, $R_4$ and $R_5$ as $C_6$-$C_{18}$alkyl are n-hexyl, n-octyl, n-nonyl, decyl, dodecyl, tetradecyl, hexadecyl or octadecyl. Alkyl groups having 8 to 18 C atoms are preferred.

Examples of $R_3$, $R_4$ and $R_5$ as substituted phenyl are tolyl, ethylphenyl, xylyl, cumyl, cymyl, cresyl, 4-methoxyphenyl, 2,4-dimethoxyphenyl, alkoxyphenyl, butoxyphenyl, p-n-octylphenyl, p-n-nonylphenyl or p-n-dodecylphenyl.

Phosphites which are very particularly suitable are trioctyl, tridecyl, tridodecyl, tritetradecyl, tristearyl, trioleyl, triphenyl, tricresyl, tris-p-nonylphenyl or tricyclohexyl phosphite, and the aryl dialkyl phosphites and the alkyl diaryl phosphites, for example phenyl didecyl, nonylphenyl didecyl, (2,4-di-tert-butylphenyl) didodecyl phosphite and (2,6-di-tert-butylphenyl) didodecyl phosphite, are particularly preferred.

Examples of metal carboxylates are the metal salts of aliphatic carboxylic acids which have 6 to 20 C atoms and are saturated, unsaturated or substituted by hydroxyl groups, such as hexanoic acid, heptanoic acid, octanoic acid, 2-ethylhexanoic acid, undecanoic acid, lauric acid, myristic acid, palmitic acid, stearic acid, 12-hydroxystearic acid, oleic acid, linoleic acid or ricinoleic acid. The metal salts of aromatic carboxylic acids, for example substituted phenylbenzoates, are also of interest. Metals from the series Ba, Sr, Ca, Mg, Zn and Cd are preferred. Examples of preferred metal carboxylates are Ca stearate or Zn stearate and Zn oleate and Ca oleate.

Suitable metal phenates are, in particular, the metal salts of phenols having 6-20 C atoms, for example alkylphenols, such as p-tert-butyl-, p-octyl-, p-nonyl- or p-dodecyl-phenol. Examples of these are Bap-tert-butylbenzoate or Ba p-n-nonylphenate.

The following other co-stabilizers are suitable:

1. Antioxidants 1.1. Alkylated monophenols, for example 2,6-di-tert-butyl-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol and 2,6-di-nonyl-4-methylphenol.

1.2. Alkylated hydroquinones, for example 2,6-di-tert-butyl-4-methoxyphenol, 2,5-di-tert-butyl-hydroquinone, 2,5-di-tert-amyl-hydroquinone and 2,6-diphenyl-4-octadecyloxyphenol.

1.3. Hydroxylated thiodiphenyl ethers, for example 2,2'-thiobis-(6-tert-butyl-4-methylphenol), 2,2'-thiobis-(4-octylphenol), 4,4'-thiobis-(6-tert-butyl-3-methylphenol) and 4,4'-thiobis-(6-tert-butyl-2-methylphenol).

1.4. Alkylidenebisphenols, for example 2,2'-methylenebis-(6-tert-butyl-4-methylphenol), 2,2'-methylenebis-(6-tert-butyl-4-ethylphenol), 2,2'-methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-di-tert-butylphenol), 2,2'-ethylidenebis-(4,6-di-tert-butylphenol), 2,2'-ethylidenebis-(6-tert-butyl-4-isobutylphenol), 2,2'-methylenebis-[6-(α-methylbenzyl)-4-nonylphenol], 2,2'-methylenebis-[6-(α, α-dimethylbenzyl)-4-nonylphenol], 4,4'-methylenebis-(2,6-ditertbutylphenol), 4,4'-methylenebis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)dicyclopentadiene and bis-[2-(3'-tert-butyl-2'-hydroxy-5'-methylbenzyl)-6-tert-butyl-4-methylphenyl]terephthalate.

1.5. Benzyl compounds, for example 1,3,5-tris-(3,5-di-tert-butyl-4-hydroxybenzyl)-2,4,6-trimethylbenzene, bis-(3,5-di-tert-butyl-4-hydroxybenzyl) sulphide, isooctyl 3,5-di-tert-butyl-4-hydroxybenzylmercaptoacetate, bis-(4-tert-butyl-3-hydroxy-2,6-dimethylbenzyl) dithiolterephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzyl phosphonate, the Ca salt of monoethyl 3,5-di-tert-butyl-4-hydroxybenzyl phosphonate and 1,3,5-tris-(3,5-dicyclohexyl-4-hydroxybenzyl) isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine and octyl N-(3,5-di-tert-butyl-4-hydroxyphenyl)-carbamate.

1.7. Esters of β-(3,5-di-tert-butyl-4-hydroxyphenyl)-propionic acid with monohydric or polyhydric alcohols, for example methanol, octadecanol, 1,6hexanediol, neopentyl glycol, thiodiethylene glycol, diethylene glycol, triethylene glycol, pentaerythritol, tris-(hydroxyethyl) isocyanurate and N,N'-bis-(hydroxyethyl)-oxamide.

1.8. Esters of β-(5-tert-butyl-4-hydroxy-3-methylphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxy)ethyl isocyanurate and N,N'-bis-(hydroxyethyl)-oxamide.

1.9. Esters of β-(3,5-dicyclohexyl-4-hydroxyphenyl)-propionic acid with monohydric or polyhydric alcohols, for example methanol, octadecanol, 1,6hexanediol, neopentyl glycol, thiodiethylene glycol, diethylene glycol, triethylene glycol, pentaerythritol, tris-(hydroxy)ethyl isocyanurate and N,N'-bis-(hydroxyethyl)-oxamide.

1.10. Amides of β-(3,5-di-tert-butyl-4-hydroxyphenyl)-propionic acid, for example N,N'-bis-(3,5 -ditert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

2. UV absorbers and light stabilizers 2.1. 2-(2'-Hydroxyphenyl)-benzotriazoles, for example the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tertbutyl-, 4'-octoxy-, 3',5'-di-tert-amyl- and 3',5'-bis-(α,α-dimethylbenzyl) derivative.

2.2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy-, and 2'-hydroxy-4,4'-dimethoxy derivative.

2.3. Esters of optionally substituted benzoic acids, for example 4-tertbutylphenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)-phenol], such as the 1:1-complex or the 1:2complex, if appropriate having additional ligands, such as n-butylamine, triethanolamine or N-cyclohexyldiethanolamine, nickel dibutyldithiocarbamate, nickel salts of monoalkyl esters of 4-hydroxy-3,5-di-tert-butylbenzylphosphonic acid, such as the methyl or ethyl ester, nickel complexes of ketoximes, such as 2-hydroxy-4-methylphenyl undecyl ketone oxime, and nickel complexes of 1-phenyl-4-lauroyl-5-hydroxypyrazole, if appropriate having additional ligands.

2.6. Sterically hindered amines, for example bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, the condensation product formed from 1-hydroxyethyl-2,2,6,6-tetramethyl-4-hydroxypiperidine and succinic acid, the condensation product formed from N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate and 1,1'-(1,2-ethanediyl)-bis-(3,3,5,5-tetramethyl-piperazinone).

2.7. Oxamides, for example 4,4'-di-octyloxyoxanilide, 2,2'-di-octyloxy-5,5'-di-tert-butyl-oxanilide, 2,2'-di-dodecyloxy-5,5'-di-tert-butyloxanilide, 2-ethoxy-2'-ethyloxanilide, N,N'-bis-(3-dimethylaminopropyl)oxamide, 2-ethoxy-5-tert-butyl-2'-ethyloxanilide and the mixture thereof with 2-ethoxy-2'-ethyl-5,4'-di-tert-butyloxanilide and mixtures of o-methoxy- and p-methoxy-di-substituted oxanilides and of o-ethoxy- and p-ethoxy-di-substituted oxanilides.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example tris-(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, tristearyl sorbityl triphosphite, tetrakis-(2,4-di-tert-butyl-phenyl) 4,4'-biphenylenediphosphonite and 3,9-bis-(2,4-di-tert-butylphenoxy)-2,4,8,10-tetraoxa-3,9-diphosphaspiro[5.5]undecane.

5. Basic co-stabilizers, for example melamine, polyvinylpyrrolidone, dicyandiamide, triallyl cyanurate, urea derivatives, hydrazine derivatives, amines, polyamides, polyurethanes, the alkali metal salts and alkaline earth metal salts of higher fatty acids, for example Ca stearate, Zn stearate, Mg stearate, Na ricinoleate and K palmitate, antimony pyrocatecholate or tin pyrocatecholate.

6. Fillers and reinforcing agents, for example calcium carbonate, silicates, glass fibres, asbestos, talc, kaolin, mica, barium sulfates, metal oxides and hydroxides, carbon black and graphite.

7. Other additives, for example plasticizers, slip agents, emulsifiers, pigments, fluorescent brighteners, fire-retarding agents, antistatic agents and blowing agents.

Preferred antioxidants are alkylated monophenols, alkylidenebisphenols and phenyl-substituted propionic acid esters, but especially 2,6-di-tert-butyl-p-cresol, 2,2-bis-(4'-hydroxyphenyl)-propane and n-octadecyl β-(3,5-di-tert-butyl-4-hydroxyphenyl)-propionate.

The thermoplastics according to the invention can be processed to give shaped articles by the shaping processes customary for them, for example by extrusion, injection moulding or calandering. Use as plastisols is also possible.

The stabilization against heat of chlorine-containing thermoplastics by means of the stabilizer mixtures according to the invention is excellent. Their content of volatile constituents and their odour are also low. In addition they are readily compatible with the customary slip agents.

The following examples serve to illustrate the invention in greater detail. Unless otherwise defined, parts are parts by weight and percentages are percentages by weight.

EXAMPLES

Example 1: Preparation of di-n-octyltin bis-[2-(2-ethylhexyloxycarbonyl)-phenylmercaptide]

A mixture of 41.6 g of dioctyltin oxide (99% content) and 61.4 g of 2-ethylhexyl thiosalicylate (99% content) is heated at 100° C. under a vacuum of 20 mbar for 45 minutes, and the water formed in the reaction is removed. Clarification by filtration is carried out when the reaction is complete. The reaction product is a yellow, oily liquid.

Refractive index $n_D^{20}$: 1.5475

Analysis % Sn: 13.3 (calculated 13.6); % S: 7.3 (calculated 7.3)

Example 2: Preparation of n-octyltin tris-[4-(ethoxycarbonyl)-phenylmercaptide]

30.9 g of 50% sodium hydroxide solution is added, at 60° C. and with vigorous stirring, to a mixture of 44.1 g of octyltin trichloride (99% content), 71.2 g of ethyl p-mercaptobenzoate, 100 ml of toluene and 50 ml of water, care being taken that the pH of the mixture does not exceed a value of 7.0 at any time. When the reaction is complete, the organic phase is removed and washed twice with water. Toluene and residual water are removed by distillation. The resulting product is a pale yellow, oily liquid.

Refractive index $n_D^{20}$: 1.6138

Analysis % Sn: 15.3 (calculated 15.3); % S: 12.1 (calculated 12.4)

Example 3: Preparation of bis-carbobutoxyethyltin bis-[2-(ethoxycarbonyl)-phenylmercaptide]

61.8 g of dicarbobutoxyethyltin dichloride (98% content) are reacted, as described in Example 2, with 49.8 g of ethyl thiosalicylate (99% content) in 43.2 g of 25% aqueous NaOH solution. The reaction product is a pale Yellow liquid.

Refractive index $n_D^{20}$: 1.5778

Analysis % Sn: 15.9 (calculated 16.1); % S: 8.6 (calculated 8.7)

Example 4: Preparation of dilauryltin bis-[2-(ethoxycarbonyl)phenyl-mercaptide]

65.1 g of dilauryltin dichloride (99% content) are reacted, as described in Example 2, with 44.9 g of ethyl thiosalicylate (99% content) in 39.0 g of 25% aqueous NaOH solution. The reaction product is a pale yellow, oily liquid.

Refractive index $n_D^{20}$: 1.5540

Analysis % Sn: 14.6 (calculated 14.5); % S: 7.8 (calculated 7.8)

Example 5: Preparation of di-n-octyltin bis-[4-(2-ethylhexyloxycarbonyl)-phenylmercaptide]

41.6 g of dioctyltin oxide (99% content) are reacted, as described in Example 1, with 61.4 g of 2-ethylhexyl p-mercaptobenzoate (99% content).

The reaction product is a pale yellow, oily liquid.

Yield: 98% of theory

Refractive index $n_D^{20}$: 1.5400

Analysis: % Sn 13.4 (calculated 13.6); % S 7.3 (calculated 7.3)

Example 6: Preparation of di-n-octyltin bis-[3-(ethoxycarbonyl)phenyl-mercaptide]

51.6 g of dioctyltin oxide (99% content) are reacted, as described in Example (1), with 51.7 g of ethyl m-mercaptobenzoate (99.5% content).

The reaction product is a pale yellow, oily liquid.

Yield: 98% of theory

Refractive index $n_D^{20}$: 1.5630

Analysis: % Sn 16.7 (calculated 16.8); % S 9.0 (calculated 9.1)

Example 7: Mixture of mono-n-octyltin and di-n-octyltin 4-ethoxycarbonylphenyl mercaptides 39.4 g of dioctyltin oxide (99% content) and 7.8 g of monooctyltin oxide (99.5% content) are reacted, analogously to Example 1, with 56.3 g of ethyl p-mercaptobenzoate (99.5% content).

The reaction product obtained was a yellow, oily liquid.

Yield: 98% of theory

Refractive index $n_D^{20}$ 1.5785

Analysis: % Sn=16.2 (calculated 16.4); % S=9.8 (calculated 9.85) Other compounds which are prepared correspondingly and by processes analogous to those described in Examples 1 to 7 are listed in a tabular summary. Like the compounds of Examples 1, 3 and 4, the compounds have the general formula $R_2Sn(S-o-C_6H_4-COOR')_2$ the meaning of R and R' for Examples 8 and 9 can be seen in Table I.

TABLE I

| No. | R | R' | $n_D^{20}$ | Description |
|---|---|---|---|---|
| 8 | n-$C_8H_{17}$ | $C_2H_5$ | 1.5724 | l, pale yellow |
| 9 | n-$C_8H_{17}$ | i-$C_4H_9$ | 1.5601 | l, pale yellow | l = liquid

Table II lists another compound, which is prepared analogously to the processes of the preceding examples. As in the preceding Examples 5 and 6, the compound has the general formula $R_2Sn(-S-p-C_6H_4-COOR')_2$ the substituents R and R' for Example 10 can be seen from Table II.

TABLE II

| No. | R | R' | $n_D^{20}$ | Description |
|---|---|---|---|---|
| 10 | n-$C_8H_{17}$ | $C_2H_5$ | 1.5693 | l, liquid, oily |

The compounds of Examples 1 to 10 are subjected to various test procedures. The results achieved can be seen in the following statements.

Stability to heat

Example 11

| Compound according to Example | TGA (1) Loss in weight (%) | | Oven test (2) | |
|---|---|---|---|---|
| | 160° C. | 200° C. | 160°/45 minutes loss in weight (colour change) | 200°/120 minutes loss in weight (colour change) |
| 1 | 0.80 | 1.3 | 2.7* (pale yellow) | 10.1* (yellow-orange) |

*Gardner colour number

Example 12

| Compound according to Example | TGA (1) Loss in weight (%) | |
|---|---|---|
| | 160° C. | 200° C. |
| 5 | 0.68 | 1.4 |

(1) Thermogravimetric analysis, heating rate 10° C./minute, inert gas atmosphere (2) Oven test: 5 g of each sample are subjected to the conditions mentioned in a circulating air drying cabinet with access of air. The loss in weight (%) and colour change of the samples, originally pale yellow, are then determined.

Assessment: For the practical operation of PVC processing the stability of the stabilizers with access of air is a decisive factor. The low loss in weight and colour change of the compounds according to the invention is evidence of their excellent stability to oxidation and hydrolysis.

Heat tests (Test of stabilizer action in PVC)

(a) Static:

The PVC, the plasticizer and the slip agent are mixed with the stabilizer or mixtures of stabilizers, milled on a roll mill at 190° C. for the periods indicated below and subjected to a static heat test. Pieces of test sheeting 0.3 mm thick are taken from the rough sheet formed. The samples of sheeting are exposed to heat at 190° C. in an oven, and the yellowing (Yellowness Index YI as specified in ASTM D 1925-70) is determined on a sample at intervals of 10 minutes. The results are shown in the tables below.

(b) Dynamic:

The dry blend is processed on the roll mill as described in (a). However, the rough sheet is not, as above, removed after it has completely gelled, but the milling process is continued until the composition is distinctly discoloured. At the intervals of time indicated in each case, pieces of sheeting are removed and their degree of yellowing is determined by the method of measurement mentioned above.

Examples 13–15: static heat test

Base formulation:

| Suspension PVC (K value 58) | 100 parts |
|---|---|
| Montan wax | 0.2 part |
| Fatty acid glycerol ester | 1.0 part |
| Stabilizer as in Table | 1.2 parts |

Milling time 5 minutes

| | | Yellowing (YI as specified in ASTM D 1925-70) Exposure time, minutes | | | | |
|---|---|---|---|---|---|---|
| Example | Stabilizer Compound according | 0 | 10 | 20 | 30 | |
| 13 | 8 | 4.0 | 6 | 15 | 42 | |
| 14 | 3 | 7.0 | 9 | 19 | 43 | |
| 15 | 4 | 4.0 | 7 | 18 | 57 | |

Example 16

Base formulation as in Examples 13-15, milling time 10 minutes

| Example | Stabilizer Compound according to Example | | Yellowing (YI as specified in ASTM D 1925-70) Exposure time, minutes | | | | |
|---|---|---|---|---|---|---|---|
| | | | 0 | 10 | 20 | 30 | 40 |
| 16 | 2 | 1.2 parts | 11 | 23 | 45 | 81 | 120 |

Example 17–23: dynamic heat test

Base formulation:

| Suspension PVC (K value 60) | 100 parts |
|---|---|
| Montan wax | 0.2 part |
| Glycerol ester | 1.0 part |
| Stabilizer | 1.2 parts |
| Milling time | see Table |

| Example | Stabilizer Compound according to Example | Yellowing (YI as specified in ASTM D 1925-70) Exposure time in minutes | | | | |
|---|---|---|---|---|---|---|
| | | 10 | 20 | 30 | 40 | 50 |
| 17 | 8 | 5.6 | 29 | 79 | 120 | |
| 18 | 10 | 21 | 33 | 109 | | |
| 19 | 6 | 28 | 36 | 44 | 141 | |
| 20 | Mixture of: 3 parts by weight of n-octyltin tris-[4-(ethoxycarbonyl)-phenyl mercaptide] and 7 parts by weight of di-n-octyltin bis-[4-(ethoxycarbonyl)-phenyl mercaptide] | 17 | 22 | 26 | 96 | 115 |
| 21 | Mixture of: 3 parts by weight of n-octyltin tris-[3-(ethoxycarbonyl)-phenyl mercaptide] and 7 parts by weight of di-n-octyltin bis-[3-(ethoxycarbonyl)-phenyl mercaptide] | 21 | 24 | 25 | 39 | 102 |
| 22 | Mixture of: 3 parts by weight of n-octyltin tris-[3-(isooctylcarbonyl)-phenyl mercaptide] and 7 parts by weight of di-n-octyltin bis-[4-(isooctylcarbonyl)-phenyl mercaptide] | 23 | 29 | 93 | 116 | |
| 23 | Mixture of: 3 parts by weight of n-octyltin tris-[3-(isooctylcarbonyl)-phenyl mercaptide] and 7 parts by weight of di-n-octyltin bis-[3-(isooctylcarbonyl)-phenyl mercaptide] | 25 | 29 | 33 | 102 | 121 |

Examples 24–26: Static heat test

| Suspension PVC (K value 70) | 100 parts |
|---|---|
| DOP | 47 parts |
| ESBO | 3 parts |
| PE wax | 0.1 part |
| Stabilizer | 1.0 part |
| Milling time | 10 minutes |

| Example | Stabilizer Compound according to Example | Yellowing (YI as specified in ASTM D 1925-70) Exposure time in minutes | | | | | | | | |
|---|---|---|---|---|---|---|---|---|---|---|
| | | 0 | 10 | 20 | 30 | 40 | 50 | 60 | 70 | 80 |
| 24 | 11 | 1.5 | 2.5 | 3.4 | 5.3 | 13 | 25 | 46 | 59 | 73 |
| 25 | 13 | 1.9 | 4.3 | 6.2 | 8.2 | 14 | 15 | 22 | 40 | 80 |
| 26 | 14 | 2.5 | 5.2 | 7.0 | 10 | 12 | 16 | 25 | 33 | 106 |

What is claimed is:

1. A compound of the formula I

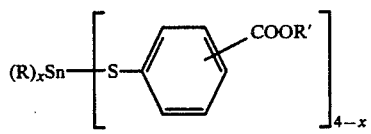

wherein R is $C_3$-$C_{14}$alkyl or $R''OOC-CH_2-CH_2-$, R' is $C_2$-$C_{12}$alkyl, cyclohexyl or benzyl, R" is $C_1$-$C_{14}$alkyl and x is 1 or 2, subject to the proviso that, if x is 1, the group COOR is not located in the ortho-position relative to the mercapto group.

2. A compound according to claim 1 of the formula

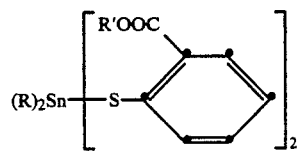

3. A compound according to claim 1, in which R is alkyl having 8 to 12 C atoms or is carbo—$C_2$—$C_5$alkoxyethyl.

4. A compound according to claim 1, in which R" is alkyl having 2 to 12 C atoms.

5. A compound according to claim 1, in which the esterified acid group in the phenyl radical is located in the ortho-position relative to the mercapto group.

6. A compound according to claim 1

$(n-C_8H_{17})_2Sn(-S-p-C_6H_4-COOC_8H_{17})_2$.

7. A method of stabilizing chlorine-containing thermoplastics by the addition of a compound of the formula I according to claim 1 to the chlorine-containing thermoplastics.

8. A method according to claim 7 of stabilizing polyvinyl chloride and polymers containing polyvinyl chloride.

9. A method according to claim 7, which embraces the use of at least two compounds of the formula I.

10. A method according to claim 9, which embraces the use of at least one monoorganotin compound and at least one diorganotin compound of the formula I according to claim 1.

11. A method according to claim 7, which embraces the use of a mixture of a diorganotin compound of the formula I according to claim 1 and a dialkyltin carboxylate.

12. A chlorine-containing thermoplastic which contains 0.1 to 5% by weight relative to the thermoplastic, of at least one compound of the formula I according to claim 1, as stabilizer.

13. A thermoplastic according to claim 12, which contains, in addition, co-stabilizers belonging to the series of the dialkyltin carboxylates in a ratio by weight of stabilizer of the compound of the formula I according to claim 1 to co-stabilizer from 60 to 40 up to 97 to 3.

14. A thermoplastic according to claim 13, which contains co-stabilizers in a ratio by weight of stabilizer to co-stabilizer from 60 to 40 up to 90 to 10.

* * * * *